United States Patent [19]
Odom et al.

[11] Patent Number: 5,950,827
[45] Date of Patent: Sep. 14, 1999

[54] INJECTOR PEN STORAGE CASE

[76] Inventors: Jeffrey L. Odom; Charlotte A. Odom, both of 7462 Quorum Dr., Baton Rouge, La. 70817

[21] Appl. No.: 09/168,713

[22] Filed: Oct. 8, 1998

[51] Int. Cl.⁶ .................................................... B65D 85/30
[52] U.S. Cl. .......................... 206/364; 206/459.1; 206/37
[58] Field of Search ...................... 206/570, 571, 206/38, 234, 459.1, 37, 37.4, 365, 364; 116/202

[56] References Cited

U.S. PATENT DOCUMENTS

| | | | |
|---|---|---|---|
| 4,250,998 | 2/1981 | Taylor | 206/570 |
| 4,401,434 | 8/1983 | Harris | 604/310 |
| 4,429,793 | 2/1984 | Ehmann | 206/570 |
| 4,446,970 | 5/1984 | Further | 206/569 |
| 5,373,940 | 12/1994 | Hillelson | 206/385 |
| 5,519,931 | 5/1996 | Reich | 206/365 X |
| 5,556,599 | 9/1996 | Ahmed | 422/102 |
| 5,775,488 | 7/1998 | Vaught | 206/37 X |

*Primary Examiner*—Jacob K. Ackun
*Attorney, Agent, or Firm*—Joseph N. Breaux

[57] ABSTRACT

An injector pen storage case for storing an injector pen, such as used by highly allergic individuals to inject epinephrine, that includes an mechanism for indicating when an injector pen housed within the storage case has leaked and is no longer usable.

1 Claim, 2 Drawing Sheets

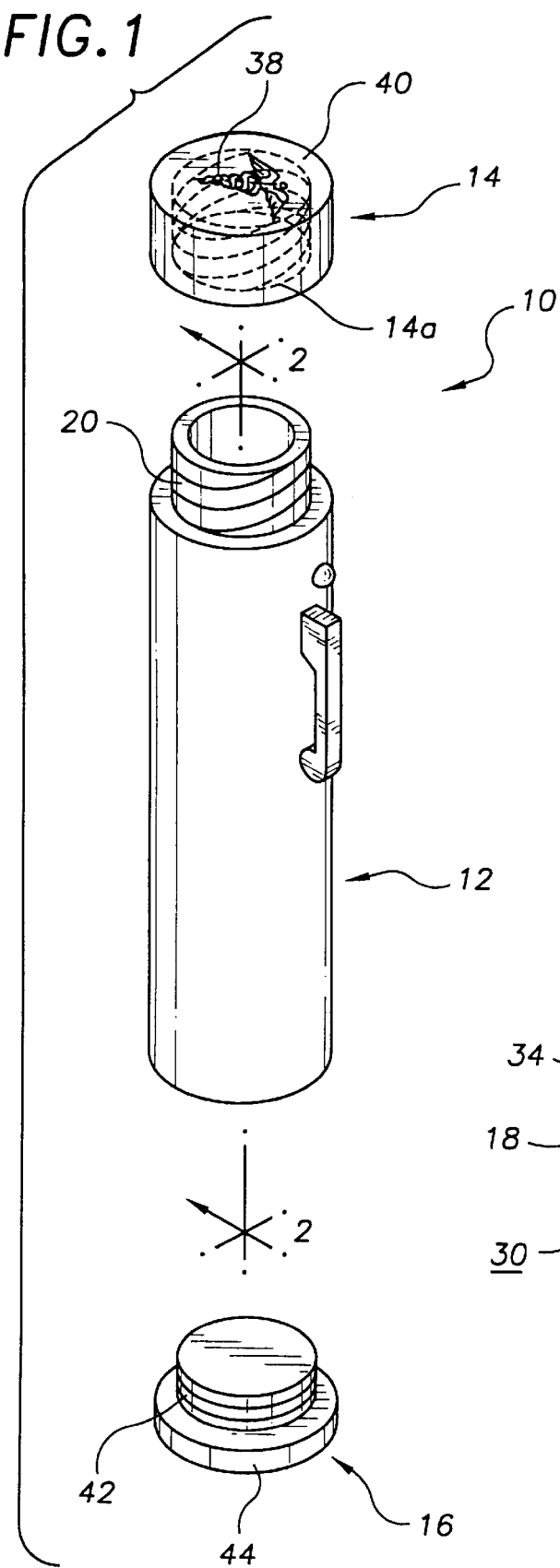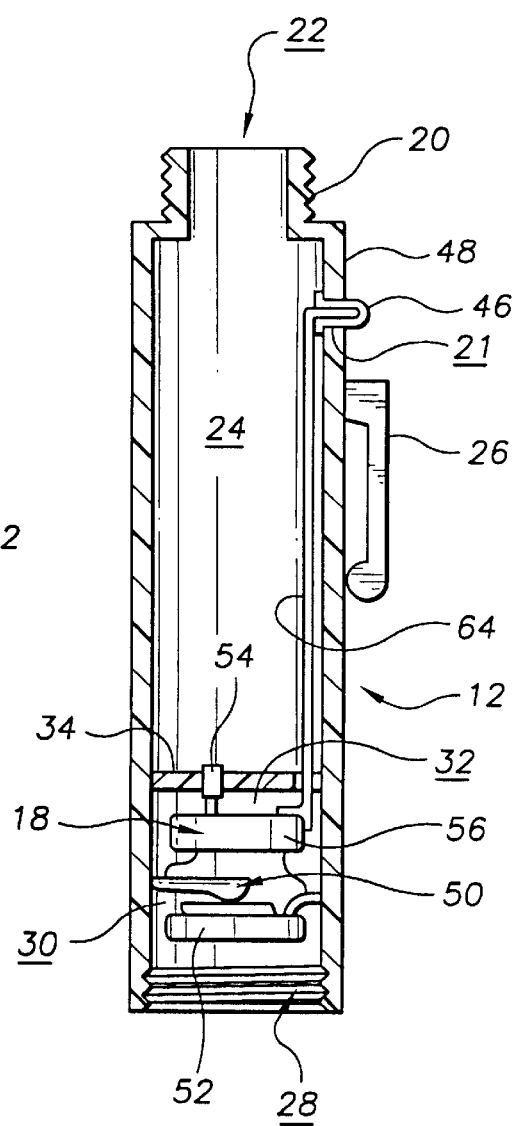

5,950,827

INJECTOR PEN STORAGE CASE

TECHNICAL FIELD

The present invention relates to carrying cases and more particularly to an injector pen storage case for storing an injector pen, such as used by highly allergic individuals to inject epinephrine, that includes an mechanism for indicating when an injector pen housed within the storage case has leaked and is no longer usable; the injector pen storage case including a main body portion, a top cap, a battery compartment cover, and a liquid detection circuit; the main body portion including a threaded neck, an access opening defined by the threaded neck, an injector pen storage chamber formed within the main body portion in connection with the access opening, a pocket clip secured to the outside of the main body portion, an internally threaded battery compartment access opening formed into a bottom end of the main body portion, a battery compartment formed with the main body portion in connection with the battery compartment access opening, a circuit compartment formed within the main body portion, a resilient divider insert positioned within the main body portion and defining a barrier between the injector pen storage chamber and the circuit compartment; the top cap is internally companionately threaded to screw down and engage the threaded neck of the main body portion and seal the access opening; the battery compartment cover includes a threaded plug portion formed on an end cap portion, the threaded plug portion being companionately threaded to screw into and seal the battery compartment access opening; the liquid detection circuit including an indicator diode extending out of a sidewall of the main body portion, a battery connector positioned within the battery compartment, a battery positioned in electrical connection with the battery connector, a liquid detecting sensor inserted through the resilient divider insert, and a digital control circuit positioned within the circuit compartment and in electrical connection with the indicator diode, the battery connector, and the liquid detecting sensor; the liquid detecting sensor including a non-conducting body, anode and cathode elements extending through the non-conducting body into opposed ends of a liquid accumulation channel formed into an exterior surface of the non-conducting body, and anode and cathode element connecting wires in connection, respectively, with the anode and the cathode; the resilient divider insert including a sensor aperture and a diode wire passage aperture formed therethrough; the liquid detecting sensor being inserted into the sensor aperture such that the liquid accumulation channel is in direct connection with the injector pen storage chamber; the digital control circuit being triggered by a closed circuit between the anode and cathode elements of the liquid detecting sensor caused by the accumulation of a conducting liquid in the liquid accumulation channel; the digital control circuit generating an illumination signal to the indicator diode upon being triggered and continuing until the digital control circuit is reset.

BACKGROUND ART

Many individuals are extremely allergic and can have life threatening allergic reactions when exposed to a particular allergen or chemical compound. Because the occurrence of the exposure cannot be predicted and, therefore, prevented, individuals suffering from extreme allergies must often carry an epinephrine injector pen for injecting themselves at the first sign of an allergic reaction. Because the injector pen may not be needed for months or years, the injector pen can become damaged and unusable when needed. It would be a benefit, therefore, to have a carrying case that could shield the injector pen from traumatic damage such as crushing and bending and, thereby, extend the useful life of an injector pen. Because, the injector pen is subject to leak, it would be a further benefit to have an injector pen storage case that included a mechanism for alerting an individual when free liquid was present within the storage case.

GENERAL SUMMARY DISCUSSION OF INVENTION

It is thus an object of the invention to provide an injector pen storage case.

It is a further object of the invention to provide an injector pen storage case having an injector pen storage chamber and that includes a mechanism for indicating the presence of a liquid within the injector pen storage chamber.

It is a still further object of the invention to provide an injector pen storage case that includes a main body portion, a top cap, a battery compartment cover, and a liquid detection circuit; the main body portion including a threaded neck, an access opening defined by the threaded neck, an injector pen storage chamber formed within the main body portion in connection with the access opening, a pocket clip secured to the outside of the main body portion, an internally threaded battery compartment access opening formed into a bottom end of the main body portion, a battery compartment formed with the main body portion in connection with the battery compartment access opening, a circuit compartment formed within the main body portion, a resilient divider insert positioned within the main body portion and defining a barrier between the injector pen storage chamber and the circuit compartment; the top cap is internally companionately threaded to screw down and engage the threaded neck of the main body portion and seal the access opening; the battery compartment cover includes a threaded plug portion formed on an end cap portion, the threaded plug portion being companionately threaded to screw into and seal the battery compartment access opening; the liquid detection circuit including an indicator diode extending out of a sidewall of the main body portion, a battery connector positioned within the battery compartment, a battery positioned in electrical connection with the battery connector, a liquid detecting sensor inserted through the resilient divider insert, and a digital control circuit positioned within the circuit compartment and in electrical connection with the indicator diode, the battery connector, and the liquid detecting sensor; the liquid detecting sensor including a non-conducting body, anode and cathode elements extending through the non-conducting body into opposed ends of a liquid accumulation channel formed into an exterior surface of the non-conducting body, and anode and cathode element connecting wires in connection, respectively, with the anode and the cathode; the resilient divider insert including a sensor aperture and a diode wire passage aperture formed therethrough; the liquid detecting sensor being inserted into the sensor aperture such that the liquid accumulation channel is in direct connection with the injector pen storage chamber; the digital control circuit being triggered by a closed circuit between the anode and cathode elements of the liquid detecting sensor caused by the accumulation of a conducting liquid in the liquid accumulation channel; the digital control circuit generating an illumination signal to the indicator diode upon being triggered and continuing until the digital control circuit is reset.

It is a still further object of the invention to provide an injector pen storage case that accomplishes some or all of the above objects in combination.

Accordingly, an injector pen storage case is provided. The injector pen storage case includes a main body portion, a top cap, a battery compartment cover, and a liquid detection circuit; the main body portion including a threaded neck, an access opening defined by the threaded neck, an injector pen storage chamber formed within the main body portion in connection with the access opening, a pocket clip secured to the outside of the main body portion, an internally threaded battery compartment access opening formed into a bottom end of the main body portion, a battery compartment formed with the main body portion in connection with the battery compartment access opening, a circuit compartment formed within the main body portion, a resilient divider insert positioned within the main body portion and defining a barrier between the injector pen storage chamber and the circuit compartment; the top cap is internally companionately threaded to screw down and engage the threaded neck of the main body portion and seal the access opening; the battery compartment cover includes a threaded plug portion formed on an end cap portion, the threaded plug portion being companionately threaded to screw into and seal the battery compartment access opening; the liquid detection circuit including an indicator diode extending out of a sidewall of the main body portion, a battery connector positioned within the battery compartment, a battery positioned in electrical connection with the battery connector, a liquid detecting sensor inserted through the resilient divider insert, and a digital control circuit positioned within the circuit compartment and in electrical connection with the indicator diode, the battery connector, and the liquid detecting sensor; the liquid detecting sensor including a non-conducting body, anode and cathode elements extending through the non-conducting body into opposed ends of a liquid accumulation channel formed into an exterior surface of the non-conducting body, and anode and cathode element connecting wires in connection, respectively, with the anode and the cathode; the resilient divider insert including a sensor aperture and a diode wire passage aperture formed therethrough; the liquid detecting sensor being inserted into the sensor aperture such that the liquid accumulation channel is in direct connection with the injector pen storage chamber; the digital control circuit being triggered by a closed circuit between the anode and cathode elements of the liquid detecting sensor caused by the accumulation of a conducting liquid in the liquid accumulation channel; the digital control circuit generating an illumination signal to the indicator diode upon being triggered and continuing until the digital control circuit is reset.

BRIEF DESCRIPTION OF DRAWINGS

For a further understanding of the nature and objects of the present invention, reference should be had to the following detailed description, taken in conjunction with the accompanying drawings, in which like elements are given the same or analogous reference numbers and wherein:

FIG. 1 is an exploded perspective view of an exemplary embodiment of the injector pen storage case of the present invention showing the main body portion including the threaded neck, the access opening defined by the threaded neck, the injector pen storage chamber in connection with the access opening, the pocket clip secured to the outside of the main body portion, and the indicator diode positioned through the main body portion; the internally threaded top cap that is companionately threaded to engage the threaded neck of the main body portion and seal the access opening; and the battery compartment cover with the threaded plug portion formed on the end cap portion.

FIG. 2 is a sectional view of the main body portion of FIG. 1 showing the threaded neck, the access opening, the injector pen storage chamber, the pocket clip, the internally threaded battery compartment access opening, the battery compartment, the circuit compartment, the resilient divider insert defining the barrier between the injector pen storage chamber and the circuit compartment, and the liquid detection circuit including the indicator diode extending out of the sidewall of the main body portion, the battery connector positioned within the battery compartment, the battery positioned in connection with the battery connector, the liquid detecting sensor inserted through the resilient divider insert, and the digital control circuit positioned within the circuit compartment.

EXEMPLARY MODE FOR CARRYING OUT THE INVENTION

Figure 3:
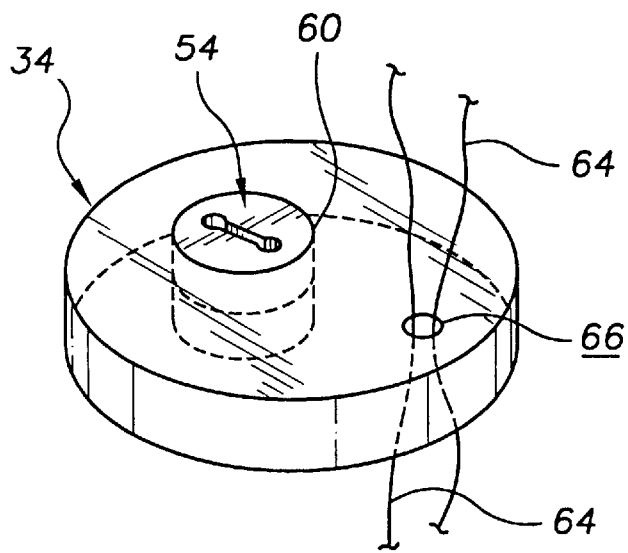
FIG. 3 is perspective view of the disk shaped resilient divider insert of FIG. 2, showing a sensor aperture and a diode wire passage aperture formed therethrough with sections of the diode connecting wires positioned through the diode wire passage aperture and the liquid detecting sensor inserted through the sensor aperture.

FIG. 1 shows an exemplary embodiment of the injector pen storage case of the present invention generally designated 10. Injector pen storage case 10 includes a main body portion, generally designated 12; a top cap, generally designated 14; a battery compartment cover, generally designated 16; and, referring now to FIG. 2, a liquid detection circuit, generally designated 18.

Main body portion 12 includes a threaded neck 20, an access opening 22, an injector pen storage chamber 24, a pocket clip 26, an internally threaded battery compartment access opening 28, a battery compartment 30, a circuit compartment 32, a diode aperture 21, and a resilient divider insert 34 positioned within main body portion 12 and defining the barrier between injector pen storage chamber 24 and circuit compartment 34. Injector pen storage chamber 24 is of sufficient size to receive completely therein a desired injector pen. Injector pen storage chamber 24 and access opening 22 are sealed by screwing, with reference back to FIG. 1, the internally, companionately threaded 14a top cap 14 down onto threaded neck 20 of main body portion 12. In this embodiment, top cap 14 has a caduceus 38 molded into the top 40 thereof.

Battery compartment cover 16 includes a threaded plug portion 42 formed on a disk shaped end cap portion 44. Threaded plug portion 44 is companionately threaded to engage and seal internally threaded seal battery compartment access opening 28 and battery compartment 30.

Referring to FIG. 2, liquid detection circuit 18 includes an indicator diode 46 that is installed through diode aperture 21 and that extends out past an outside surface 48 of main body portion 12; a battery connector 50 positioned within battery compartment 30; a battery 52 positioned in connection with battery connector 50; a liquid detecting sensor 54 inserted through resilient divider insert 34; and a digital control circuit 56 positioned within circuit compartment 32.

Referring to FIG. 3, liquid detecting sensor 54 is inserted through a sensor aperture 60 provided through resilient divider insert 34. The electrical connection between indicator diode 46 (FIG. 2) and digital control circuit 56 (FIG. 2) is accomplished by wires 64 positioned through a diode wire passage aperture 66 that is formed through resilient divider insert 34.

Figure 4:
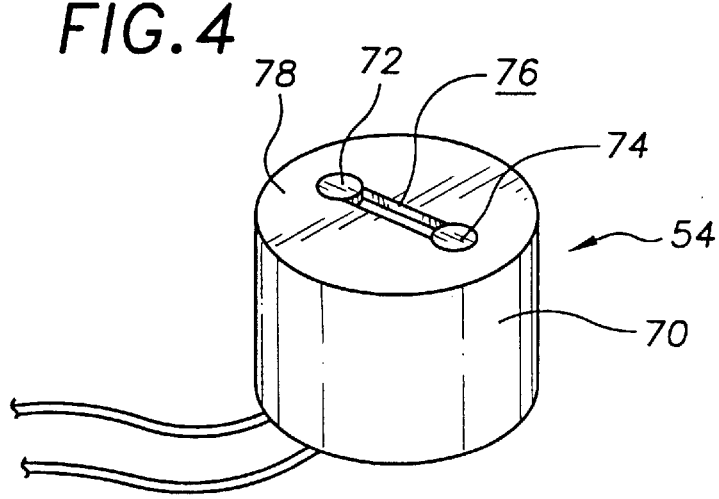
FIG. 4 is a perspective view of the liquid detecting sensor in isolation showing the non-conducting cylinder shaped body, the anode and cathode elements extending into opposed ends of the liquid accumulation channel, and the anode and cathode element connecting wires.

Referring to FIG. 4, liquid detecting sensor includes a non-conducting cylinder shaped body 70 and anode and cathode elements 72,74 extending into opposed ends of a liquid accumulation channel 76 formed into an exterior surface 78 of non-conducting body 70. Liquid accumulation channel 76 is sized such that when a quantity of a conducting liquid, such as liquid epinephrine, accumulates therein, a closed circuit is created through the conducting fluid between anode and cathode elements 72,74. Non-conducting body 70 is sized to fit into and seal sensor aperture 60 (FIG. 3) of resilient divider insert 34 (FIG. 3). With general reference to FIGS. 2–4, resilient divider insert 34 is inserted within body portion 12 such that liquid accumulation channel 76 is in direct connection with injector pen storage chamber 24.

Figure 5:
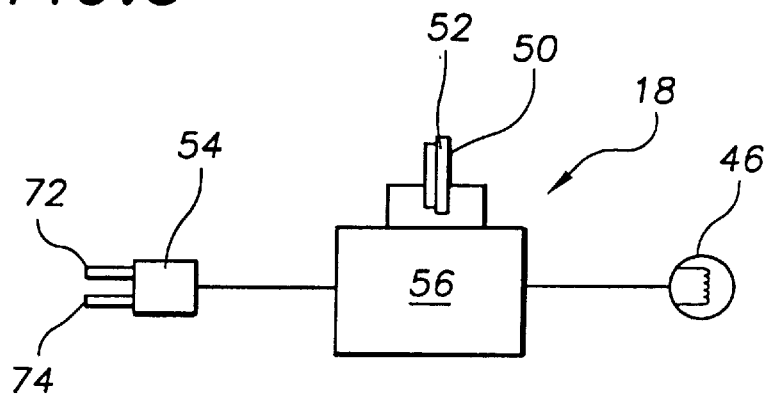
FIG. 5 is schematic diagram showing the digital control circuit in electrical connection with the liquid detecting sensor, the indicator diode, and the battery connector, the digital control circuit being triggered by a closed circuit between the anode and cathode elements of the liquid detecting sensor caused by the accumulation of a conducting liquid in the liquid accumulation channel, the digital control circuit generating a blink signal to the indicator diode upon being triggered and continuing until the digital control circuit is reset.

Referring to FIG. 5, digital control circuit 56 of liquid detecting circuit 18 is constructed of conventional digital components and is in electrical connection with liquid detecting sensor 54, indicator diode 46, and battery connector 50. Digital control circuit 56 is triggered by a closed circuit between anode and cathode elements 72,74 of liquid detecting sensor 54 which is created as previously discussed by the accumulation of a conducting liquid in liquid accumulation channel 76 (FIG. 4). Once triggered, digital control circuit 56 generates an illumination signal, in this case a blink signal, to indicator diode 46 causing it to blink. The illumination signal continues to indicator diode 46 until digital control circuit 56 is reset by disconnecting battery 52 from battery connector 50. Blinking indicator diode 46 is used to attract the attention of a user and alert him/her that a leak has occurred.

It can be seen from the preceding description that an injector pen storage case has been provided that has an injector pen storage chamber and includes a mechanism for indicating the presence of a liquid within the injector pen storage chamber; and that includes a main body portion, a top cap, a battery compartment cover, and a liquid detection circuit; the main body portion including a threaded neck, an access opening defined by the threaded neck, an injector pen storage chamber formed within the main body portion in connection with the access opening, a pocket clip secured to the outside of the main body portion, an internally threaded battery compartment access opening formed into a bottom end of the main body portion, a battery compartment formed with the main body portion in connection with the battery compartment access opening, a circuit compartment formed within the main body portion, a resilient divider insert positioned within the main body portion and defining a barrier between the injector pen storage chamber and the circuit compartment; the top cap is internally companionately threaded to screw down and engage the threaded neck of the main body portion and seal the access opening; the battery compartment cover includes a threaded plug portion formed on an end cap portion, the threaded plug portion being companionately threaded to screw into and seal the battery compartment access opening; the liquid detection circuit including an indicator diode extending out of a sidewall of the main body portion, a battery connector positioned within the battery compartment, a battery positioned in electrical connection with the battery connector, a liquid detecting sensor inserted through the resilient divider insert, and a digital control circuit positioned within the circuit compartment and in electrical connection with the indicator diode, the battery connector, and the liquid detecting sensor; the liquid detecting sensor including a non-conducting body, anode and cathode elements extending through the non-conducting body into opposed ends of a liquid accumulation channel formed into an exterior surface of the non-conducting body, and anode and cathode element connecting wires in connection, respectively, with the anode and the cathode; the resilient divider insert including a sensor aperture and a diode wire passage aperture formed therethrough; the liquid detecting sensor being inserted into the sensor aperture such that the liquid accumulation channel is in direct connection with the injector pen storage chamber; the digital control circuit being triggered by a closed circuit between the anode and cathode elements of the liquid detecting sensor caused by the accumulation of a conducting liquid in the liquid accumulation channel; the digital control circuit generating an illumination signal to the indicator diode upon being triggered and continuing until the digital control circuit is reset.

It is noted that the embodiment of the injector pen storage case described herein in detail for exemplary purposes is of course subject to many different variations in structure, design, application and methodology. Because many varying and different embodiments may be made within the scope of the inventive concept(s) herein taught, and because many modifications may be made in the embodiment herein detailed in accordance with the descriptive requirements of the law, it is to be understood that the details herein are to be interpreted as illustrative and not in a limiting sense.

What is claimed is:

1. An injector pen storage case comprising:

a main body portion;

a top cap;

a battery compartment cover; and a liquid detection circuit;

said main body portion including a threaded neck, an access opening defined by a threaded neck, an injector pen storage chamber formed within said main body portion in connection with said access opening, a pocket clip secured to an outside surface of said main body portion, an internally threaded battery compartment access opening formed into a bottom end of said main body portion, a battery compartment formed with said main body portion in connection with said battery compartment access opening, a circuit compartment formed within said main body portion, a resilient divider insert positioned within said main body portion and defining a barrier between said injector pen storage chamber and said circuit compartment;

said top cap being internally companionately threaded to screw down and engage said threaded neck of said main body portion and seal said access opening;

said battery compartment cover including a threaded plug portion formed on an end cap portion, said threaded plug portion being companionately threaded to screw into and seal said battery compartment access opening;

said liquid detection circuit including an indicator diode extending out of said outside surface of said main body portion, a battery connector positioned within said battery compartment, a battery positioned in electrical connection with said battery connector, a liquid detecting sensor inserted through said resilient divider insert, and a digital control circuit positioned within said circuit compartment and in electrical connection with said indicator diode, said battery connector, and said liquid detecting sensor;

said liquid detecting sensor including a non-conducting body, anode and cathode elements extending through said non-conducting body into opposed ends of a liquid accumulation channel formed into an exterior surface of said non-conducting body, and anode and cathode element connecting wires in connection, respectively, with said anode element and said cathode element;

said resilient divider insert including a sensor aperture and a diode wire passage aperture formed therethrough;

said liquid detecting sensor being inserted into said sensor aperture of said resilient divider insert such that said liquid accumulation channel is in direct connection with said injector pen storage chamber;

said digital control circuit being triggered by a closed circuit between said anode element and said cathode element of said liquid detecting sensor caused by an accumulation of a conducting liquid in said liquid accumulation channel;

said digital control circuit generating an illumination signal to said indicator diode upon being triggered and continuing until said digital control circuit is reset.

\* \* \* \* \*